United States Patent [19]

Grote

[11] 4,169,292
[45] Oct. 2, 1979

[54] ARTIFICIAL MIDDLE EAR AND EAR CANAL PROSTHESIS

[76] Inventor: Johannes J. Grote, Bolwerkshof, Lerop, St. Odilienberg, Netherlands

[21] Appl. No.: 851,435

[22] Filed: Nov. 14, 1977

[30] Foreign Application Priority Data

Nov. 15, 1976 [NL] Netherlands ........................ 7612657

[51] Int. Cl.² .............................................. A61F 1/18
[52] U.S. Cl. ................................................... 3/1.9
[58] Field of Search ........................................ 3/1, 1.9

[56] References Cited

U.S. PATENT DOCUMENTS

| | | | |
|---|---|---|---|
| 1,045,917 | 12/1912 | Valiquet | 3/1 UX |
| 3,909,852 | 10/1975 | Homsy | 3/1.9 |
| 3,931,648 | 1/1976 | Shea, Jr. | 3/1.9 |
| 3,992,725 | 11/1976 | Homsy | 3/1.9 X |
| 4,052,754 | 10/1977 | Homsy | 3/1.9 |

FOREIGN PATENT DOCUMENTS 187940  12/1966  U.S.S.R. ............................................ 3/1

OTHER PUBLICATIONS

Science Illustrated, Mar. 1948, pp. 30-31; "New Artificial Eardrums are made from Soft Plastic".
Homsy, et al., "Porous Implant Systems for Prosthesis Stabilization," Reprint from *Clinical Orthopedics*, No. 89, Nov.-Dec.-1972, pp. 220-235.

*Primary Examiner*—Clifford D. Crowder
*Attorney, Agent, or Firm*—Omri M. Behr

[57] ABSTRACT

An artificial middle ear prosthesis may be used to replace the ear structure from the bony ear canal up to the oval window of the vestibule. The artificial middle ear includes a tube to replace at least part of the bony ear canal, an annulus to connect an artificial ear drum to the tube, a complex structure to replace the hammer and anvil of a human patient and a piston means connected to the complex structure to replace at least part of the stirrup. According to one embodiment the piston may directly connect the complex hammer/anvil structure to the remaining portion of the oval window of the vestibule. According to another embodiment, the piston may be terminated in a cup shaped socket which will cradle the remaining structure of a stirrup. The bony ear canal tube, the umbo section connecting the complex hammer/anvil structure to the ear drum and the end of the piston directly contacting the stirrup or the oval window are preferably coated with a microporous biocompatible material such as Proplast. The ring or annulus is preferably formed from polytetrafluorethylene or a perfluorinated ethylene propylene polymer. The invention makes it possible to totally eradicate chronic otitis media without sparing the bony ear canal or bony annulus, by replacing the diseased tissues with the prosthesis described.

19 Claims, 5 Drawing Figures

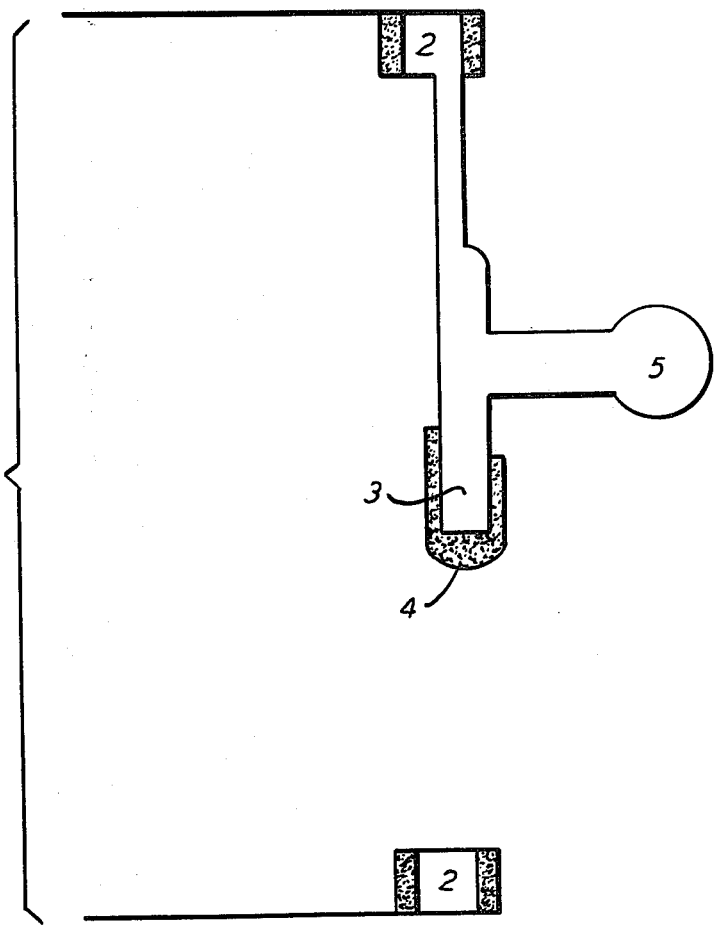
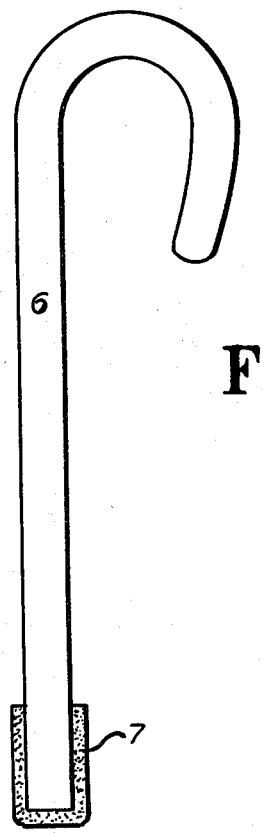
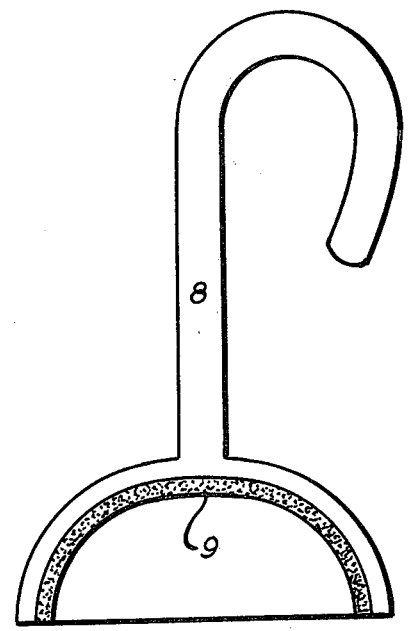

ARTIFICIAL MIDDLE EAR AND EAR CANAL PROSTHESIS

BACKGROUND OF THE INVENTION

1. Field of the Invention

This invention relates to an artificial middle ear and ear canal prosthesis.

2. Description of the Prior Art

The human middle ear system, which is responsible for the transmission of sound vibrations to the inner ear is describable as follows: "A bony canal ends in a bony annulus or ring. A drum membrane is fixed in the ring. The middle ear bone chain is connected via the hammer to the drum membrane that makes contact with the inner ear via the anvil and stirrup. The contact of the stirrup with the oval window provides for the transmission of sound vibration in the inner ear. The efficient transmission of sound depends upon the viability of the drum membrane and the effective contact of middle ear chain with the oval window."

The efficient transmission of sound can be destroyed or substantially reduced by chronic otitis media. This disease can destroy part or all of the total middle ear system. It may even destroy parts of the bony external ear canal. The inner ear, the facial nerve and the brain may also run the risk of being attacked.

In view of the foregoing it is desirable for a surgeon to remove the entire diseased area in order to avoid reoccurence. Such drastic surgery will frequently result in a substantial hole in the mastoid.

Attempts to reconstruct the middle ear system were begun approximately 20 years ago. Since then many systems have been developed in order to restore sound conduction. Autologous materials were originally used for reconstruction purposes. Unfortunately, up until the present, a total reconstruction has been impossible.

Towards the end of the late 1960's inert materials such as Teflon and polyethylene were employed as prosthesis in order to restore the middle ear bony chain. These prosthesis were placed between the preserved portions of the patient's middle ear. Generally the initial results were satisfactory but eventually the prosthesis were extruded by the middle ear. Teflon is still the preferred material as the substitute for the stirrup.

Subsequently a method was developed which eradicated the disease and kept intact the bony canal and the bony annulus. This technique made it possible to do implantations of homologous middle ears. These implantations consisted of a drum membrane, hanmer, anvil and stirrup. That was the first time that the induction system of the middle ear was restored in toto.

Another problem that arose was the desirability of preserving an intact bony ear canal and bony annulus. Eventually, the reconstruction of the middle ear was made secondary to the definite sanitation of the chronic otitis media. Debate still continues about the recurrence of chronic otitis media. The results obtained with regard to sound conduction by a homologous middle ear structure are varying. In the development of otology the use of biocompatible materials was not begun until 1970. At that time an ossiclar replacement prosthesis was developed by Charles A Hamsy in cooperation with John Shea. A description of a device can be found in U.S. Pat. No. 3,909,852. The prosthesis described in that patent was developed to replace the bony middle ear chain. Fixation of the device was made possible by the use of a micropourous implant material which has the characteristics of promoting living tissue. The prosthesis described in U.S. Pat. No. 3,909,852 is characterized by only a single columella which is fixed at the ends thereof to the ear drum and oval window. The use of the prosthesis is predicated on the existence of a normal ear drum having an intact canal wall and a totally eradicated middle ear cleft.

SUMMARY OF THE INVENTION

Briefly described the invention comprises a totally artificial middle ear. With this invention it is possible to totally remove the disease in the middle ear, in a safe way, because it is then not necessary to save the bony annulus or bony canal wall. Another embodiment provides for an artificial middle ear system which is analogous to the human middle ear system in function and size. The invention described is transportable and is attached to the ear structure at the same locations as the normal middle ear structure would be located. According to the apparatus and method described it is possible to perform a safe and complete sanitation of the middle ear without causing restoration, because the invention allows the middle ear system to be rebuilt in its totality including the annulus and missing part of the bony ear canal.

BRIEF DESCRIPTION OF THE DRAWINGS

FIG. 3 is a cross section of the artificial total middle ear prosthesis as shown in FIG. 2.

FIG. 4A illustrates a piston similar to that described in U.S. Pat. No. 3,909,852 which is used to contact the oval window in the situation where the stirrup is missing.

FIG. 4B is an alternative embodiment illustrating a cup piston designed to contact the remains of an existing stirrup which may still be located in situ in the patient.

DETAILED DESCRIPTION OF THE INVENTION

During the course of this description like numbers will be used to indicate like elements according to the different views of the invention.

Figure 1:
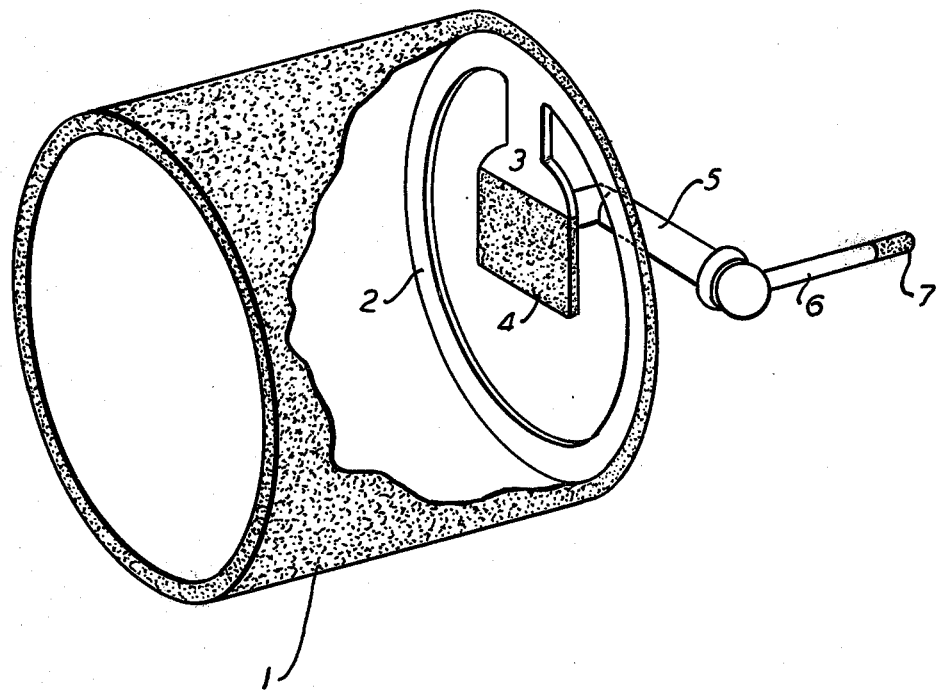
FIG. 1 is a perspective view of the total middle ear prosthesis according to the preferred embodiment of the present invention.
Figure 2:
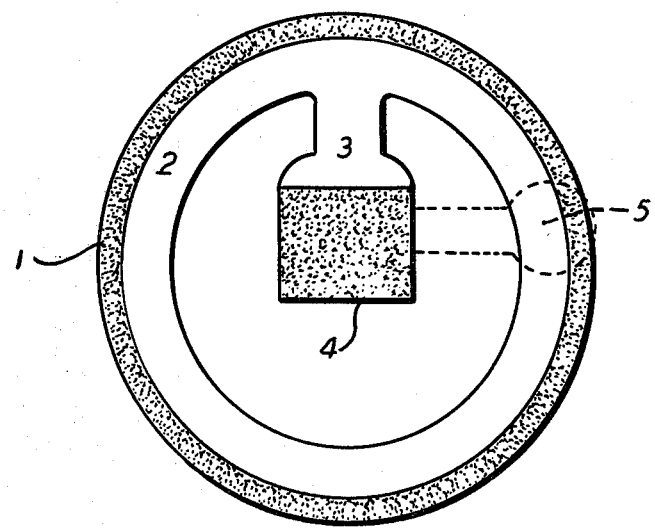
FIG. 2 is an end view of the annulus and the replacements of the middle ear bony chain as connected to the annulus.

As shown in FIG. 1 of the drawings the total artificial inner ear prosthesis includes a tube of biocompatible microporous material 1 which replaces the missing part of the external bony ear canal. The bony ear canal preferably is formed from a biocompatible, microporous material such as Proplast, a material manufactured by Vitek Incorporated of Houston, Tex. Proplast generally is a microporous polyetrafluoroethylene with a pyrolitic graphite coating. The tube is normally placed in close contact with the remaining portions of the bony ear canal. An annulus 2 of biocompatible material is affixed at one end of the tube 1. The annulus replaces the annulus around the normal ear drum. According to the preferred embodiment of the invention the annulus is formed from Teflon. Teflon ® is a trademark of the DuPont Company. The Teflon may be a polytetrafluoroethylene and sold under the mark Teflon "TFE" or a perfluorinated ethylene propylene polymer and sold under the mark Teflon "FEP" by the DuPont Company. As will be clear from the specification, Teflon ® is the preferred material for certain parts of the invention, however, there are other known biocompatible implantation materials which may be used as well.

A complex structure of the same material is attached to annulus 2 to replace the hammer and anvil of a typical human ear. The attachment is made in such a fashion as to provide relative mobility. A coating of biocompatible microporous material is placed at the location 4 where the drum membrane is connected to the umbo. The dimensions of the hammer 3 and anvil 5 complex correlate generally with the dimensions of the same elements as found in the normal middle ear so that the free end of the complex is locatable just above the oval window on the vestibule.

There are two possible problems which may be encountered at this juncture. In the first case there may be no stirrup structure left and the oval window may be empty. In that situation a piston 6 similar to that described in U.S. Pat. No. 3,909,852 and formed from a biocompatible material such as Teflon may be hung in a groove at the free end of the prosthesis. The other end of the piston 6 would then be covered with a biocompatible microporous material 7 such as Proplast in order to allow that end to be affixed to the remnants of the oval window. This may be accomplished in the same way as described in U.S. Pat. No. 3,909,852.

In the second situation there may be a portion of a mobile stirrup structure left attached to the oval window. In such a situation a cup piston 8 of a suitable biocompatible material such as Teflon is hung on a groove at the free end of the prosthesis. The cup portion of that piston 8 is placed over top of the remaining stirrup structure. A coating of a suitable biocompatible microporous material 9 such as Proplast is applied to the interior of the cup portion of the cup piston 8 so as to allow the fixation of the artificial middle ear chain to the existing stirrup.

A suitable biocompatible microporous implant material such as Proplast that will promote the ingrowth of living tissue into the pores of the material, may be used on the bony ear canal replacement structure 1, on the hammer 3 at location 4, at the end of piston element 6 at location 7 or on the interior of the cup section 9 of the cup piston 8. The ear drum material in the artificial middle ear is repaired or replaced with any autologous material such as normally used in a myringoplasty in man.

The proportions of the prosthesis just described are comparable with those found in the human middle ear. The dimensions of the elements of the prosthesis and their related materials are as follows:

The microporous tube 1 preferably comprises a material such as Proplast and has an average outer diameter of 8.0 mm and an average inner diameter of 6.5 mm.

The biocompatible annulus 2 preferably formed from Teflon has an average outer diameter of approximately 7.4 mm and an average inner diameter of 5.4 mm, giving an average thickness of 1.0 mm.

The handle section of the hammer 3/anvil 5 complex includes two parts. The first part is the part which connects to the annulus which has a length of approximately 1.0 mm, a width of 0.5 mm and a thickness of 0.25 mm. The second part of the handle comprises the umbo 4 which is connected to the ear drum. It has an approximately average length of 1.7 mm, an average width of 1.5 mm and an average thickness of 0.5 mm. The umbo 4 is covered with a sleeve or coating of a microporous biocompatible material such as Proplast as previously described. The anvil section 5 of the middle ear chain is connected with the umbo 4 at a location which is 1.35 mm from the inner circle of annulus 2. The same connection is approximately 0.35 mm from the top of the umbo 4. The depth of the first part of the middle ear 5 is approximately 2.0 mm. The diameter of the same section has an average dimensions of 0.5 mm. The length of element 5 from the umbo connection to the free end knob is approximately 2.5 mm. The thickness of the free end is about 0.5 mm.

The piston portions which may be connected to the free ends of the anvil section 5 can be formed in one of the following two possible ways. According to an embodiment such as illustrated in U.S. Pat. No. 3,909,852 the piston connection 6 could have a length of approximately 6 mm with the free end thereof which makes contact with the oval window having a covering of a microporous biocompatible material such as Proplast.

According to a second embodiment the piston could comprise a Teflon cup arrangement 8 having the cup at one end and a hook at the other which would hang over the knob protrusion on the anvil section 5. The length including the cup of the second embodiment would be approximately 4.0 mm with a cup height of 1.5 mm and a cup width of 1.5 mm. The inside of the cup is preferably covered by a small piece of microporous biocompatible material 9 such as Proplast.

The structure and materials described above are the preferred form of the present invention but other materials with the same biocompatibility and in growth stimulation capacity may be used. The dimensions of the elements previously described may vary, but tend to average out to the figures given. The size of the elements and the invention as a whole are comparable with the dimensions of similar elements in the normal human middle ear. In addition, the compliance of the prosthesis must be comparable with that of the human middle ear system. The materials used in the prosthesis must also be suitable for undergoing some form of sterilization. Typically, the sterilization process would take place in a steam autoclave.

From the foregoing it can be seen that an artificial total middle ear and ear canal prosthesis such as described can be implanted as a substitution for the missing middle ear and ear canal of a human patient. The invention described provides for a mobile and flexible sound transmission system in which the prosthesis can be securely attached to parts of the living body at specific locations. By use of the prosthesis described, it is possible to totally eradicate chronic otitis media in a safe way without having to spare the bony annulus or bony ear canal.

While the invention has been described with reference to a preferred embodiment thereof and its best use, it will be understood by those of ordinary skill in the art that various different changes may be made to the parts and materials described without departing from the spirit and scope of the invention.

I claim:

1. An artificial middle ear apparatus for in vivo implantation comprising:
   A. a first portion including;
      (a) a tube means of microporous biocompatible material for replacing removed portions of the bony external ear canal;
      (b) a ring means of biocompatible material attached to said tube means for replacing the bony annulus of the ear drum and for supporting an ear drum membrane;

(c) a complex means of biocompatible material for replacing the hammer and anvil complex of a human patient; and B. a second portion including; a piston means for replacing at least part of the stirrup of a human ear, said piston means having one end thereof operably coupled to said complex means and the other end thereof adapted to be attached to the remaining portion of the middle ear system.

2. An artificial middle ear according to claim 1 wherein said complex means comprises:

(a) an elongated hammer handle portion affixed to said ring on one end thereof with its free end extending towards the center of said ring and generally in the same plane therewith;

(b) a paddle shaped hammer affixed proximate the free end of said hammer handle and generally in the same plane therewith, and (c) an anvil means having a first portion extending outwardly from said tube means and generally perpendicular thereto and including a second elongated portion affixed at one end to said first portion and extending at a generally right angle to said first portion and parallel to the plane of said hammer and said ring.

3. An artificial middle ear according to claim 1 wherein said second elongated portion of said anvil means is provided with a groove at the free end thereof and said elongated piston means one end is receivable in said groove and cooperates therewith to provide free movement therebetween.

4. An artificial middle ear according to claim 1 wherein said piston means other end is adapted to be directly attachable to a portion of the oval window of a middle ear.

5. The apparatus of claim 1 wherein said piston means is attachable at one end thereof directly to a portion of the oval window of a middle ear.

6. The apparatus of claim 5 wherein the end of said piston means which is attachable to said portion of said oval window is covered with a microporous biocompatible implant material.

7. The apparatus of claim 1 wherein said piston means includes a cup at one end thereof adapted to cradle the remains of the stirrup of a human ear.

8. The apparatus of claim 7 wherein said cup is covered by a microporous biocompatible implant material for promoting ingrowth of living tissue therein.

9. The apparatus of claim 8 wherein the end of said piston means furtherest removed from said cup is shaped in the form of a hook which is receivable in a groove on a portion of said complex means.

10. The apparatus of claim 1 wherein a microporous biocompatible material is applied to at least three locations of said apparatus including to the tube means, to the point of connection between the complex means and the ear drum membrane and to the free end of said piston means.

11. The apparatus of claim 1 wherein said ring means is formed from a polytetrafluoroethylene material.

12. The apparatus of claim 1 wherein said ring means comprises a high molecular weight polyethyelene.

13. The apparatus of claim 1 wherein said ring means comprises a perfluorinated ethylene propylene polymer.

14. The apparatus of claim 1 wherein the dimensions of the ring means, complex means and piston means are approximately the same as the bony ear structure, hammer/anvil structure and stirrup structure respectively of the human middle ear.

15. An artificial middle ear for in vivo implantation comprising:

(a) a tube means of microporous biocompatable material for replacing removed portions of the bony external ear canal;

(b) a ring means of biocompatible material attached to said tube means for replacing the bony annulus of the ear drum and for supporting an ear drum membrane;

(c) a complex means of biocompatible material for replacing the hammer and anvil complex of a human patient, said complex means including;

(i) an elongated hammer handle portion affixed to said ring on one end thereof with its free end extending towards the center of said ring and generally in the same plane therewith;

(ii) a paddle shaped hammer affixed proximate the free end of said hammer handle and generally in the same plane therewith, and (iii) anvil means having a first portion extending outwardly from said tube means and generally perpendicular thereto and including a second elongated portion affixed at one end to said first portion and extending at a generally right angle to said first portion and parallel to the plane of said hammer and said ring;

(d) elongated piston means for replacing at least part of the stirrup of a human ear, said piston means having one end thereof operably coupled to the free end of said second portion; and said elongated piston means other end being adapted to be attached to the remaining portion of the interior ear system.

16. An artificial middle ear according to claim 15 wherein said second elongated portion of said anvil means is provided with a groove at the free end thereof and said elongated piston means one end is receivable in said groove and cooperates therewith to provide free movement therebetween.

17. An artificial middle ear according to claim 15 wherein said piston means other end is adapted to be directly attachable to a portion of the oval window of a middle ear.

18. An artificial middle ear according to claim 15 wherein said piston means other end, a portion of said paddle shaped hammer, and said tube means are coated with a microporous biocompatable material.

19. An artificial middle ear according to claim 15 wherein said piston means other end includes a cup adapted to cradle the remains of the stirrup of a human ear.

* * * * *

UNITED STATES PATENT AND TRADEMARK OFFICE
CERTIFICATE OF CORRECTION

PATENT NO. : 4,169,292
DATED : October 2, 1979
INVENTOR(S) : Johannes J. Grote

It is certified that error appears in the above-identified patent and that said Letters Patent are hereby corrected as shown below:

In the Claims

Claim 1. Column 5, line 3; after "material" insert the following --attached to said ring means--.

Signed and Sealed this

Eighteenth Day of March 1980

[SEAL]

Attest:

SIDNEY A. DIAMOND

Attesting Officer   Commissioner of Patents and Trademarks